(12) United States Patent
Liu et al.

(10) Patent No.: US 10,100,044 B2
(45) Date of Patent: Oct. 16, 2018

(54) METHODS FOR PREPARING BREXPIPRAZOLE, KEY INTERMEDIATES THEREOF AND SALTS THEREOF

(71) Applicants: SUZHOU VIGONVITA LIFE SCIENCES CO., LTD., Jiangsu (CN); TOPHARMAN SHANGHAI CO., LTD., Shanghai (CN); SHANGHAI INSTITUTE OF MATERIA MEDICA, CHINESE ACADEMY OF SCIENCES, Shanghai (CN)

(72) Inventors: Zheng Liu, Shanghai (CN); Chunhui Wu, Shanghai (CN); Yongjian Liu, Shanghai (CN); Rongxia Zhang, Shanghai (CN); Yang He, Shanghai (CN); Guanghui Tian, Shanghai (CN); Jingshan Shen, Shanghai (CN)

(73) Assignees: Suzhou Vigonvita Life Sciences Co., Ltd., Jiangsu (CN); Topharman Shanghai Co., Ltd., Shanghai (CN); Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 15/030,331

(22) PCT Filed: Oct. 20, 2014

(86) PCT No.: PCT/CN2014/000921
§ 371 (c)(1),
(2) Date: Apr. 18, 2016

(87) PCT Pub. No.: WO2015/054976
PCT Pub. Date: Apr. 23, 2015

(65) Prior Publication Data
US 2016/0272624 A1  Sep. 22, 2016

(30) Foreign Application Priority Data
Oct. 18, 2013 (CN) .......................... 2013 1 0493206

(51) Int. Cl.
*C07D 333/70* (2006.01)
*C07D 409/12* (2006.01)
*C07D 333/54* (2006.01)

(52) U.S. Cl.
CPC ......... *C07D 409/12* (2013.01); *C07D 333/54* (2013.01); *C07D 333/70* (2013.01)

(58) Field of Classification Search
None
See application file for complete search history.

(56) References Cited

U.S. PATENT DOCUMENTS

| 4,977,154 A | * | 12/1990 | Sanchez | C07D 215/56 514/253.04 |
| 5,436,246 A | | 7/1995 | Bernotas et al. | |
| 2007/0259877 A1 | * | 11/2007 | Dean | C07D 207/27 514/252.12 |
| 2017/0158680 A1 | * | 6/2017 | Jiang | C07D 409/12 |

FOREIGN PATENT DOCUMENTS

| WO | 2006/112464 A1 | 10/2006 |
| WO | 2009/128537 A1 | 10/2009 |
| WO | 2013/015456 A1 | 1/2013 |
| WO | WO-2015131856 A1 * | 9/2015 |

OTHER PUBLICATIONS

Senet et al. J.Org.Chem. 49, 2081-2082 (1984).*
Machine Translation for Application No. CN 201310493206.8 (Oct. 18, 2013).*
International Search Report dated Jan. 27, 2015 from Application No. PCT/CN2014/000921.
International Search Report dated Jun. 20, 2016 from Application No. PCT/CN2014/000921.
Gerard P. Moloney, et al., "Synthesis and Serotonergic Activity of Variously Substituted (3-amido) phenylpiperazine Derivatives and Benzothiophene-4-piperazine Derivatives: Novel Antagonists for the Vascular 5-HT1B Receptor", European Journal of Medicinal Chemistry, vol. 39, 2004 Elsevier, pp. 305-321.

* cited by examiner

*Primary Examiner* — Emily A Bernhardt
(74) *Attorney, Agent, or Firm* — Baker & Hostetler LLP

(57) ABSTRACT

The present invention relates to the methods for preparing brexpiprazole, the analogs, key intermediates, and salts thereof, specifically, the present invention relates to a new method for preparing brexpiprazole, the analogs, key intermediates, and salts thereof, and the key intermediates, and salts thereof provided during the preparation. The preparation method has a mild reaction condition, stable intermediate, easy operation, and uses cheap and easy-to-get reagents, thus it saves the synthesis cost, shortens the production cycle, improves the yield and product quality, and is suitable for mass production.

15 Claims, No Drawings

METHODS FOR PREPARING BREXPIPRAZOLE, KEY INTERMEDIATES THEREOF AND SALTS THEREOF

CROSS-REFERENCE TO RELATED APPLICATIONS

This application is a National Stage of International Patent Application No. PCT/CN2014/000921, filed Oct. 20, 2014 and claims priority to foreign application CN 201310493206.8, filed Oct. 18, 2013, the contents of which are incorporated herein by reference in their entirety.

FIELD OF THE INVENTION

The present invention belongs to the field of pharmaceutical chemistry, particularly, relates to the methods for preparing brexpiprazole, the analogs, key intermediates, and salts thereof, also relates to novel compounds provided during the preparation.

BACKGROUND OF THE INVENTION

Brexpiprazole (Brexpiprazole, Code: OPC-34712) is a new generation of anti-psychotic drug candidates developed by Otsuka Pharmaceutical Co., Ltd., it takes effect on several receptors, i.e., it is the dopamine D2 receptor partial agonist (improving positive and negative symptoms, cognitive disorder and depressive symptoms), 5-HT2A receptor antagonist (improving negative symptoms, cognitive function disorder, symptoms of depression, insomnia), aI adrenergic receptor antagonists (improving the positive symptoms of schizophrenia), 5-hydroxytryptamine uptake/reuptake inhibitors (improving depressive symptoms), a 5-HT1A partial agonist (having anxiolytic and antidepressant activity) and 5-HT7 antagonists (adjusting body temperature, circadian rhythm, learning and memory, sleep) at the same time. Currently, a Phase III clinical trial for adjuvant treatment of severe depression (MIDD) is conducted in the United States and Europe; a Phase III clinical trial for the treatment of schizophrenia is conducted in the United States, Europe and Japan; meanwhile, a Phase II clinical trial for Adult ADHD (attention deficit hyperactivity disorder) is conducted in the United States.

A preparation route of brexpiprazole is disclosed in the PCT application WO2006112464 A1 by Otsuka Pharmaceutical Co., Ltd. as shown in Scheme 1, the disadvantage of this route is that by-products that cannot be easily separated are produced in the first step of the reaction, intermediates with high purity cannot be easily obtained even by column chromatography. Thus it suffered from reduced purity and yield of the final product brexpiprazole.

Scheme 1:

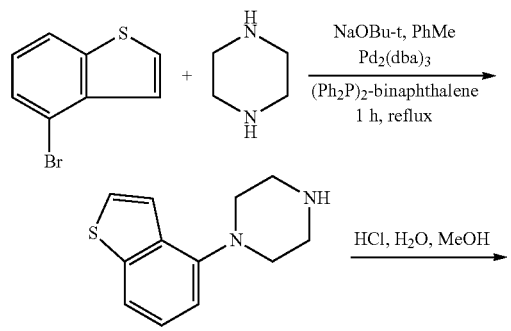

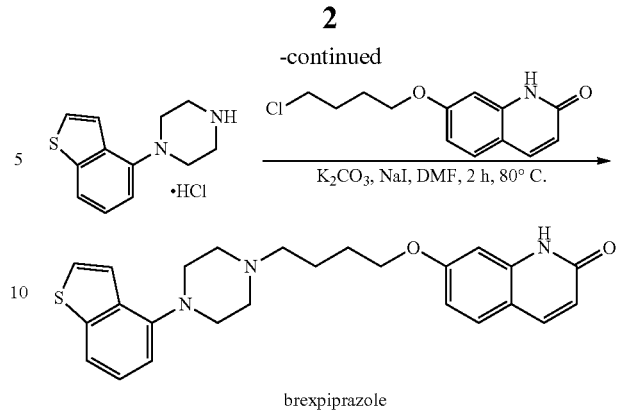

brexpiprazole

Then, another preparation route of this reaction is disclosed in the PCT application WO2013015456 A1 by Otsuka Pharmaceutical Co., Ltd. as shown in Scheme 2, the reagents used in the route are relatively expensive, so the disadvantage of the route is costly, environmentally unfriendly and not suitable for industrial production.

Scheme 2:

There are disadvantages of highcost, formation of impurities hard to separate for the above preparation method. Thus it is necessary to find a new route which is economic, practical and environmentally friendly, so as to improve process stability, reduce the cost and improve the product quality.

SUMMARY OF THE INVENTION

In response to these disadvantages, it is an object of the present invention to provide a new method for preparing brexpiprazole, the analogs, key intermediates and salts thereof with simple operation, high yield, low cost, environmentally friendly and suitable for industrial mass production.

It is another object of the present invention to provide novel compounds and salts thereof during the preparation.

In order to achieve the above object, the present invention provides compounds of formula I as shown in the following structure:

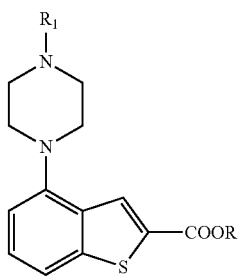

wherein, R is linear or branched C1 to C6 alkyl, benzyl, preferably, R is linear or branched C1 to C4 alkyl group, most preferably, R is methyl, ethyl or t-butyl;

R1 is

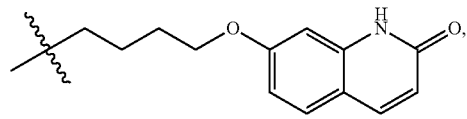

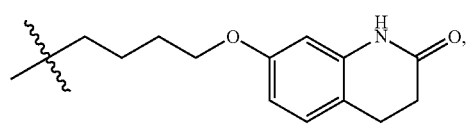

acyl-based amino-protecting groups (e.g. formyl

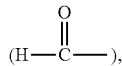

acetyl, propionyl, benzoyl, haloacetyl, phthaloyl), or alkoxycarbonyl-based amino-protecting groups (e.g. t-butoxycarbonyl, benzyloxycarbonyl, 9-fluorenyl methoxycarbonyl); the haloacetyl group is fluoroacetyl, bromoacetyl, chloroacetyl or iodoacetyl; preferably, R₁ is selected from

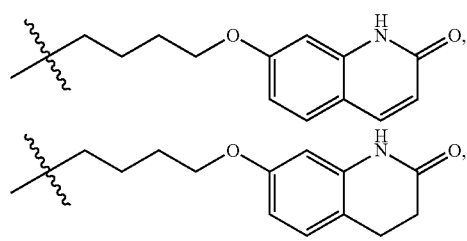

formyl, acetyl and t-butoxycarbonyl;

The present invention further provides a method for preparing a compound as shown in formula I, where the compound of formula II is reacted with a thioglycollic acid ester compound, obtaining the compound of the formula I, as shown in Scheme 3, Scheme 3:

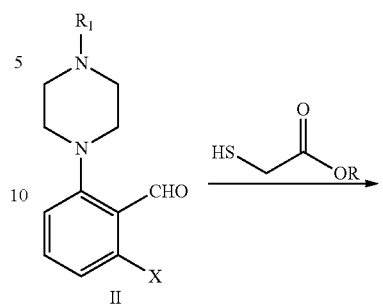

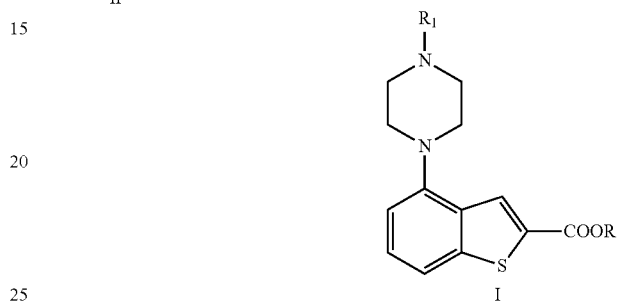

wherein, X is halogen, such as fluorine, chlorine, bromine, iodine; the definition of R and R₁ are the same as that in the above compound of the formula I;

The above reaction is conducted in the presence of a base, in particular, it is conducted in the presence of an inorganic base (e.g. sodium hydroxide, potassium hydroxide, strontium hydroxide, lithium hydroxide, barium hydroxide, calcium hydroxide, cesium hydroxide, sodium bicarbonate, potassium bicarbonate, potassium carbonate, sodium carbonate, strontium carbonate, cesium carbonate, sodium sulfide, sodium hydride, etc.) or an organic base (e.g., sodium alkoxide, potassium alkoxide, butyl lithium, 1,8-diazabicyclo[5,4,0]undec-7-ene (DBU), pyridine, quinoline, 4-dimethylaminopyridine (DMAP) or an organic amine, etc.), wherein, said sodium alkoxide may be sodium methoxide, sodium ethoxide, sodium propoxide, sodium isopropoxide, sodium n-butoxide, sodium tert-butoxide and the like; said potassium alkoxide may be potassium methoxide, potassium ethoxide, potassium propoxide, potassium isopropoxide, potassium n-butoxide, potassium tert-butoxide and the like, the organic amine may be triethylamine, diethylamine, tri-n-butylamine, tripropylamine, diisopropylamine, diisopropylethylamine, etc., preferably, the base may be an inorganic bases, such as sodium hydroxide, potassium hydroxide, lithium hydroxide, sodium bicarbonate, potassium bicarbonate, potassium carbonate, sodium carbonate, strontium carbonate, sodium sulfide, sodium hydride, or organic bases, such as sodium methoxide, sodium ethoxide, potassium t-butoxide, triethylamine, diethylamine, diisopropylamine or diisopropylethylamine;

The above reaction is conducted in a suitable solvent, the solvent is one or more selected from the group consisting of water, C1-C5 lower alcohol (such as methanol, ethanol, n-propanol, isopropanol, n-butanol, isobutanol, tert-butanol, n-pentanol, isopentanol, ethylene glycol, propylene glycol, glycerol), N,N-dimethylformamide (DMF), dimethyl sulfoxide (DMSO), tetrahydrofuran (THF), acetonitrile, dioxane, N-methylpyrrolidone, dichloromethane, chloroform, ethylene glycol dimethyl ether, diethylene glycol dimethyl ether or ethylene glycol monomethyl ether, and the like, preferably, the solvent is one or more selected from the group consisting of water, methanol, ethanol, N,N-dimethylformamide (DMF), dimethylsulfoxide (DMSO), tetrahydrofuran (THF), acetonitrile, dioxane or ethylene glycol dimethyl ether; the reaction time is 1 hour to 24 hours, preferably 2 hours to 12 hours. The reaction temperature is 0° C. to 150° C., preferably from room temperature to 100° C.

In order to achieve the above object, the present invention further provides compounds of formula III as shown in the following structure:

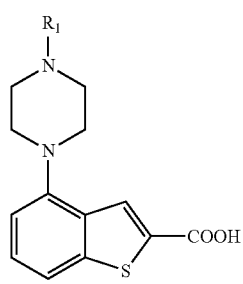

III wherein, $R_1$1 is

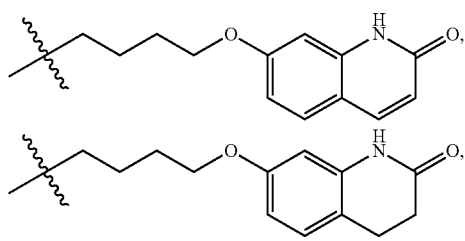

acyl-based amino-protecting groups (e.g. formyl, acetyl, propionyl, benzoyl, haloacetyl, phthaloyl), or alkoxycarbonyl-based amino-protecting groups (e.g. t-butoxycarbonyl, benzyloxycarbonyl, 9-fluorenyl methoxycarbonyl); the haloacetyl group is fluoroacetyl, bromoacetyl, chloroacetyl or iodoacetyl;

preferably, $R_1$ is

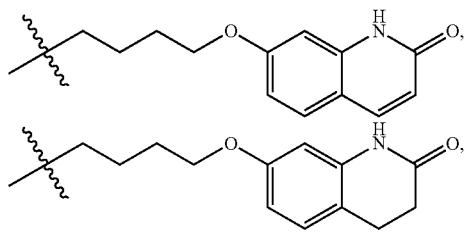

formyl, acetyl or t-butoxycarbonyl;

The present invention further provides a method for preparing a compound as shown in formula III, where the compound of formula II is reacted with thioglycollic acid obtaining the compound of the formula III, as shown in Scheme 4, Scheme 4:

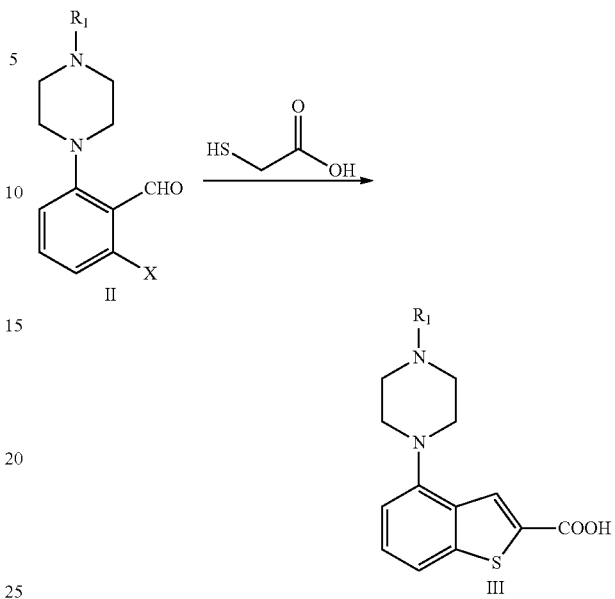

wherein, X is fluorine, chlorine, bromine or iodine; the definition of $R_1$ is the same as that in the above compound of the formula I;

The above reaction is conducted in the presence of a base, in particular, it is conducted in the presence of an inorganic base (e.g. sodium hydroxide, potassium hydroxide, strontium hydroxide, lithium hydroxide, barium hydroxide, calcium hydroxide, cesium hydroxide, sodium bicarbonate, potassium bicarbonate, potassium carbonate, sodium carbonate, strontium carbonate, cesium carbonate, sodium sulfide, sodium hydride, etc.) or an organic base (e.g., sodium alkoxide, potassium alkoxide, butyl lithium, 1,8-diazabicyclo[5,4,0]undec-7-ene (DBU), pyridine, quinoline, 4-dimethylaminopyridine (DMAP) or an organic amine, etc.), wherein, said sodium alkoxide may be sodium methoxide, sodium ethoxide, sodium propoxide, sodium isopropoxide, sodium n-butoxide, sodium tert-butoxide and the like; said potassium alkoxide may be potassium methoxide, potassium ethoxide, potassium propoxide, potassium isopropoxide, potassium n-butoxide, potassium tert-butoxide and the like, the organic amine may be triethylamine, diethylamine, tri-n-butylamine, tripropylamine, diisopropylamine, diisopropylethylamine, etc., preferably, the base may be an inorganic bases, such as sodium hydroxide, potassium hydroxide, lithium hydroxide, sodium bicarbonate, potassium bicarbonate, potassium carbonate, sodium carbonate, strontium carbonate, sodium sulfide, sodium hydride, or organic bases, such as sodium methoxide, sodium ethoxide, potassium t-butoxide, triethylamine, diethylamine, diisopropylamine or diisopropylethylamine;

The above reaction is conducted in a suitable solvent, the solvent is one or more selected from the group consisting of water, C1-C5 lower alcohol (such as methanol, ethanol, n-propanol, isopropanol, n-butanol, isobutanol, tert-butanol, n-pentanol, isopentanol, ethylene glycol, propylene glycol, glycerol), N,N-dimethylformamide (DMF), dimethyl sulfoxide (DMSO), tetrahydrofuran (THF), acetonitrile, dioxane, N-methylpyrrolidone, dichloromethane, chloroform, ethylene glycol dimethyl ether, diethylene glycol dimethyl ether or ethylene glycol monomethyl ether, and the like, preferably, the solvent is one or more selected from the group consisting of water, methanol, ethanol, N,N-dimethylformamide (DMF), dimethylsulfoxide (DMSO), tetrahydrofuran (THF), acetonitrile, dioxane or ethylene glycol dimethyl ether; the reaction time is 1 hour to 24 hours, preferably 2 hours to 12 hours. The reaction temperature is 0° C. to 150° C., preferably from room temperature to 100° C.

The present invention further relates to the following compounds:

Compound of Formula IV:

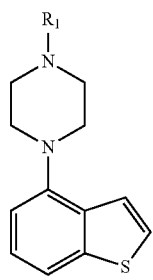

IV wherein, $R_1$ is acyl-based amino-protecting groups (e.g. formyl, acetyl, propionyl, benzoyl, haloacetyl, phthaloyl), or alkoxycarbonyl-based amino-protecting groups, e.g. benzyloxycarbonyl, 9-fluorenyl methoxycarbonyl; the haloacetyl group is fluoroacetyl, bromoacetyl, chloroacetyl or iodoacetyl; preferably, $R_1$ is formyl or acetyl group;

and a compound of formula V and salts thereof:

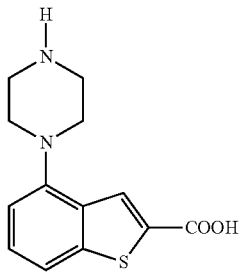

V wherein the salt is one selected from the group consisting of hydrochloride, sulfate, phosphate, nitrate, acetate, hydrobromide, hydroiodide, perchlorate, trichloroacetate and trifluoroacetate.

The present invention further provides a method for preparing a compound of formula IV, said method comprises the step to obtain the compound of formula III by the hydrolysis reaction of the compound of formula I or by the Scheme 4 from the compound of formula II, followed by the decarboxylation step to give a compound of formula IV, said method is shown in Scheme 5:

Scheme 5:

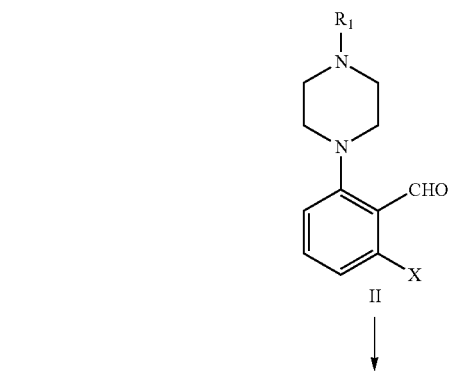

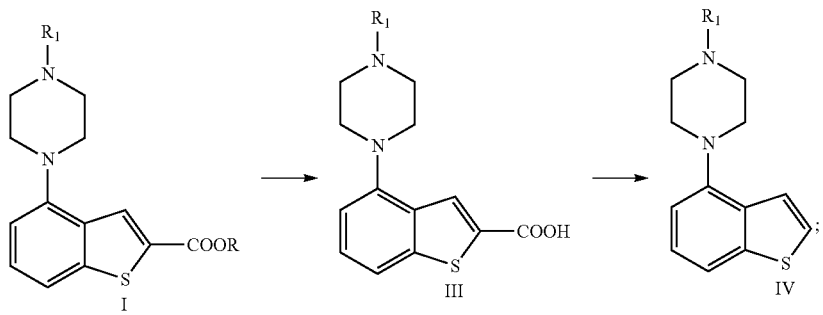

wherein, X is fluorine, chlorine, bromine or iodine; the definition of $R_1$ and R are the same as that in the above compound of the formula I; The present invention also provides a method for preparing key intermediates of Brexpiprazole or the salts thereof, the method is shown in Scheme 6:

or preparing the compound of formula VI or the salts thereof by simultaneously conducting decarboxylation and removal of the amino-protecting groups from the compound of formula III;

or preparing the compound of formula V or the salts thereof by simultaneously conducting hydrolysis and Scheme 6:

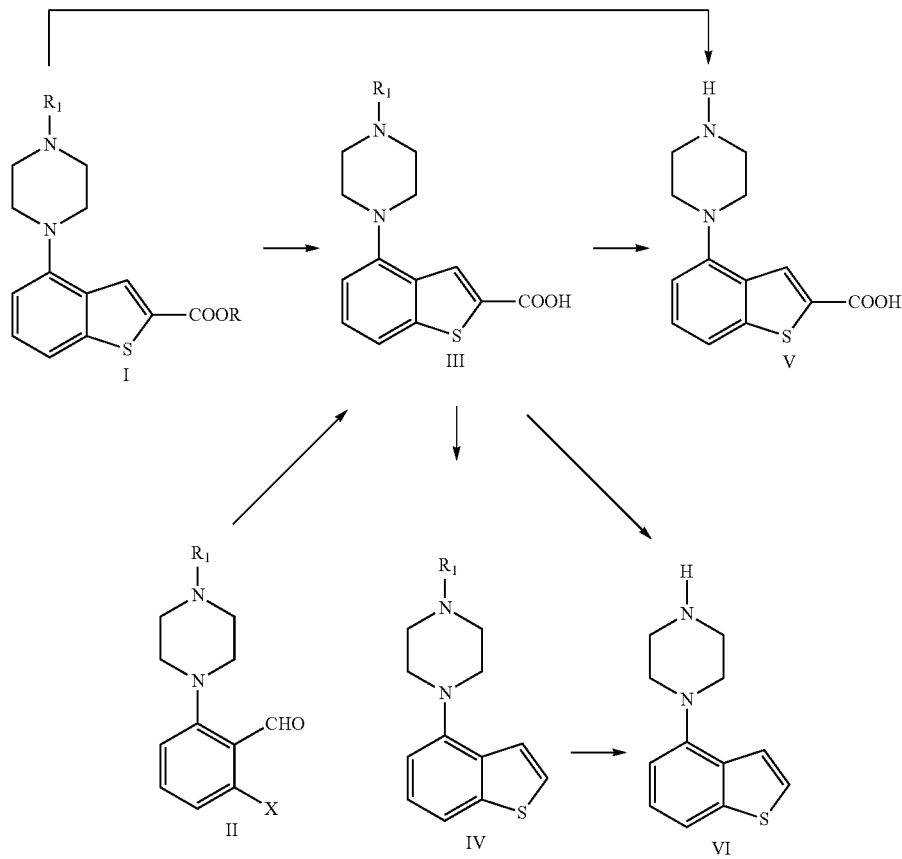

wherein, $R_1$ is acyl-based amino-protecting groups (e.g. formyl, acetyl, propionyl, benzoyl, haloacetyl, phthaloyl), or alkoxycarbonyl-based amino-protecting groups (e.g. tert-butoxycarbonyl, benzyloxycarbonyl, 9-fluorenyl methoxycarbonyl); the haloacetyl group is fluoroacetyl, bromoacetyl, chloroacetyl or iodoacetyl; preferably, $R_1$ is a formyl, acetyl group or tert-butoxycarbonyl; X is fluorine, chlorine, bromine or iodine;

R is linear or branched C1 to C6 alkyl, benzyl, preferably, R is linear or branched C1 to C4 alkyl group, more preferably, R is methyl, ethyl or t-butyl;

Specifically, the invention includes the following steps:

preparing the compound of formula III by the hydrolysis reaction of the compound of formula I, or by the Scheme 4 from the compound of formula II, then producing a compound of formula IV by decarboxylating of formula III, finally, preparing the key intermediate of Brexpiprazole (compound as shown in formula VI) or the salts thereof by removing the amino-protecting groups;

or preparing the compound of formula V or the salts thereof firstly by removing the amino-protecting groups from the compound of formula III, then preparing the compound of formula VI or the salts thereof by decarboxylating;

removal the amino-protecting groups under the acidic conditions from the compound of formula I, then preparing the compound of formula VI or the salts thereof by decarboxylating;

wherein, the salts of the compounds of formulae V and VI are one selected from the group consisting of hydrochloride, sulfate, phosphate, nitrate, acetate, hydrobromide, hydroiodide, perchlorate, trichloroacetate and trifluoroacetate, the above-described salts can be alkalized to obtain the compound of formulae V and VI as required.

In scheme 5 or scheme 6, the hydrolysis reaction may be conducted under acidic conditions, said acid may be organic acids or inorganic acids, such as one or more selected from sulfuric acid, hydrochloric acid, gaseous hydrogen chloride, hydrobromic acid, hydroiodic acid, phosphoric acid, nitric acid, acetic acid, trichloroacetic acid, trifluoroacetic acid, perchloric acid and the like, but is not limited to the above-mentioned acids; the hydrolysis reaction may also be conducted in the presence of a base, in particular, it is conducted in the presence of an inorganic base (e.g. sodium hydroxide, potassium hydroxide, strontium hydroxide, lithium hydroxide, barium hydroxide, calcium hydroxide, cesium hydroxide, sodium bicarbonate, potassium bicarbonate, potassium carbonate, sodium carbonate, strontium carbonate, cesium carbonate, sodium hydride, etc.) or an organic base (e.g., sodium alkoxide, potassium alkoxide, butyl lithium, potassium acetate, sodium acetate, 1,8-diazabicyclo[5,4,0]undec-7-ene (DBU), pyridine, quinoline, 4-dimethylaminopyridine (DMAP) or an organic amine, etc.), wherein, said sodium alkoxide may be sodium methoxide, sodium ethoxide, sodium propoxide, sodium isopropoxide, sodium n-butoxide, sodium tert-butoxide and the like; said potassium alkoxide may be potassium methoxide, potassium ethoxide, potassium propoxide, potassium isopropoxide, potassium n-butoxide, potassium tert-butoxide and the like, the organic amine may be triethylamine, diethylamine, tri-n-butylamine, tripropylamine, diisopropylamine, diisopropylethylamine, etc., preferably, the base is an inorganic bases, such as sodium hydroxide, potassium hydroxide or lithium hydroxide; The hydrolysis reaction is conducted in a suitable solvent, the solvent is one or more selected from the group consisting of water, $C_1$ to $C_5$ lower alcohol (such as methanol, ethanol, n-propanol, isopropanol, n-butanol, isobutanol, tert-butanol, n-pentanol, isopentanol, ethylene glycol, propylene glycol, glycerol), N,N-dimethylformamide (DMF), N,N-dimethylacetamide, dimethyl sulfoxide (DMSO), tetrahydrofuran (THF), acetonitrile, dioxane, morpholine, N-methylpyrrolidone, dichloromethane, chloroform, ethylene glycol dimethyl ether, diethylene glycol dimethyl ether or ethylene glycol monomethyl ether, and the like, preferably, the solvent is one or more selected from the group consisting of water, methanol, ethanol, tetrahydrofuran (THF), dioxane; the reaction temperature is 0° C. to 200° C., preferably 100° C.; the reaction time is 10 minutes to 24 hours, preferably 0.5 hours to 10 hours;

The decarboxylation reaction may be conducted with or without the presence of a catalyst, said catalyst is selected from copper, copper chromite, cuprous oxide, cupric oxide, chromium trioxide, cuprous bromide, cuprous chloride, ferrous chloride, ferric chloride, cupric carbonate, cupric sulfate, basic cupric carbonate, silver acetate, calcium oxide, calcium hydroxide, 1,8-diazabicyclo[5,4,0]undec-7-ene (DBU), 1,5-diazabicyclo[4.3.0]non-5-ene (DBN), aluminum oxide, preferably is one or more selected from copper, copper chromite, cuprous oxide, cupric oxide, chromium trioxide, 1,8-diazabicyclo[5,4,0]undec-7-ene (DBU) or aluminum oxide; or the decarboxylation is conducted in the presence of silver carbonate and acetic acid; the solvent for decarboxylation reaction may be one or more selected from the group consisting of quinoline, isoquinoline, N-methylpyrrolidone (NMP), quinoxaline, ethylene glycol dimethyl ether, diphenyl ether, biphenyl, ethylene glycol, diethylene glycol, diethylene glycol dimethyl ether, dibutyl ether, toluene, xylene, mesitylene, hexanol, heptanol, N,N-dimethyl formamide, dimethyl sulfoxide, dioxane, N,N-dimethylacetamide, 1,3-dimethyl-2-imidazolidinone, pyridine, preferably one or more from quinoline, quinoxaline, ethylene glycol dimethyl ether, N,N-dimethylformamide, dimethylsulfoxide, dioxane or the N,N-dimethylacetamide; and the reaction temperature is from room temperature to 300° C., preferably 120-250° C.; the reaction time is 5 minutes to 18 hours.

The removal of amino-protecting group is conducted in the presence of an acid, wherein the acid is selected from the group consisting of hydrochloric acid, gaseous hydrogen chloride, sulfuric acid, phosphoric acid, nitric acid, acetic acid, hydrobromic acid, hydriodic acid, perchloric acid, trichloroacetic acid or trifluoroacetic acid; The reaction solvent is one or more selected from water, dioxane, methanol, ethanol, n-propanol, isopropanol, tert-butanol, diethyl ether, N-methylpyrrolidone, tetrahydrofuran, acetonitrile, methylene chloride, chloroform, N,N-dimethylformamide, ethyl acetate, propyl acetate or butyl acetate, or the above acid may be used as a reaction solvent, without adding other solvent; the reaction temperature is 0° C. to 150° C., preferably the reaction temperature is 100° C.; the reaction time is 0.5 to 24 hours, preferably 1 to 12 hours;

The one-step method which simultaneously conduct the decarboxylation and removal of amino-protecting group is conducted in the presence of an acid, wherein the acid is one or more selected from the group consisting of hydrochloric acid, gaseous hydrogen chloride, sulfuric acid, phosphoric acid, nitric acid, acetic acid, hydrobromic acid, hydriodic acid, perchloric acid, trichloroacetic acid or trifluoroacetic acid; the reaction solvent is one or more selected from water, dioxane, methanol, ethanol, n-propanol, isopropanol, tert-butanol, diethyl ether, N-methylpyrrolidone, tetrahydrofuran, acetonitrile, methylene chloride, chloroform, N,N-dimethylformamide, ethyl acetate, propyl acetate or butyl acetate, or the above acid may be used as a reaction solvent, without adding other solvent; the reaction temperature is 0° C. to 150° C., preferably from room temperature to 100° C.; the reaction time is 0.5 to 24 hours, preferably 1 to 12 hours; alternatively, when $R_1$ is alkoxycarbonyl-based amino-protecting groups (e.g. tert-butoxycarbonyl, benzyloxycarbonyl, 9-fluorenyl methoxycarbonyl), the one-step method which simultaneously conduct the decarboxylation and removal of amino-protecting group may be conducted with or without the presence of a catalyst, said catalyst is one or more selected from copper, copper chromite, cuprous oxide, cupric oxide, chromium trioxide, cuprous bromide, cuprous chloride, ferrous chloride, ferric chloride, cupric carbonate, cupric sulfate, basic cupric carbonate, silver acetate, calcium oxide, calcium hydroxide, 1,8-diazabicyclo[5,4,0] undec-7-ene (DBU), 1,5-diazabicyclo[4.3.0]non-5-ene (DBN), aluminum oxide, preferably is one or more selected from copper, copper chromite, cuprous oxide, cupric oxide, chromium trioxide, 1,8-diazabicyclo[5,4,0]undec-7-ene (DBU) or aluminum oxide; or the reaction is conducted in the presence of silver carbonate and acetic acid; the reaction solvent may be one or more selected from the group consisting of quinoline, isoquinoline, N-methylpyrrolidone (NMP), quinoxaline, ethylene glycol dimethyl ether, diphenyl ether, biphenyl, ethylene glycol, diethylene glycol, diethylene glycol dimethyl ether, dibutyl ether, toluene, xylene, mesitylene, hexanol, heptanol, N,N-dimethyl formamide, dimethyl sulfoxide, dioxane, N,N-dimethylacetamide, 1,3-dimethyl-2-imidazolidinone, pyridine; preferably one or more from quinoline, quinoxaline, ethylene glycol dimethyl ether, N,N-dimethylformamide, dimethylsulfoxide, dioxane or the N,N-dimethylacetamide; and the reaction temperature is from room temperature to 300° C., preferably 120-250° C.; the reaction time is 5 minutes to 18 hours.

In the step of simultaneously conducting the hydrolysis reaction and removal of amino-protecting group under acidic conditions, said acid may be organic acids or inorganic acids, such as one or more selected from sulfuric acid, hydrochloric acid, gaseous hydrogen chloride, hydrobromic acid, hydroiodic acid, phosphoric acid, nitric acid, acetic acid, trichloroacetic acid, trifluoroacetic acid, perchloric acid and the like, but is not limited to the above-mentioned acids; the reaction solvent is one or more selected from the group consisting of water, $C_1$ to $C_5$ lower alcohol (such as methanol, ethanol, n-propanol, isopropanol, n-butanol, isobutanol, tert-butanol, n-pentanol, isopentanol, ethylene glycol, propylene glycol, glycerol), N,N-dimethylformamide (DMF), N,N-dimethylacetamide, dimethyl sulfoxide (DMSO), tetrahydrofuran (THF), acetonitrile, dioxane, morpholine, N-methylpyrrolidone, ethyl acetate, dichloromethane, and the like, or the above acid may be used as a reaction solvent, without adding other solvent; the reaction temperature is 0° C. to 200° C., preferably from room temperature to 100° C.; the reaction time is 0.5 to 24 hours, preferably 1 hours to 12 hours.

TECHNICAL EFFECT

The present invention has the following advantages:
When $R_1$ is selected from acyl-based amino-protecting groups (e.g. formyl

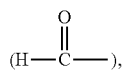

acetyl, propionyl, benzoyl, haloacetyl, phthaloyl), or alkoxycarbonyl-based amino-protecting groups (e.g. tert-butoxycarbonyl, benzyloxycarbonyl, 9-fluorenyl methoxycarbonyl), especially when $R_1$ is preferably formyl, acetyl, or tert-butoxycarbonyl, the cost of the reagent is low, and the reaction conditions for removing these protecting groups is mild, e.g., under acidic conditions, so as to directly obtain the stable salt form of the compound of formula V and VI type, which avoids the further salifying step of unstable freebase, thus reducing one reaction step. And the whole process for removing the amino-protecting group does not need expensive reagents and special reaction equipment. U.S. Pat. No. 5,436,246 discloses the case in which $R_1$ is benzyl, but the debenzylation reaction conditions is harsh, which require expensive palladium reagents and special reaction kettle, thus it is costly and relatively dangerous.

By contrast, the method for the present invention is easy to operate, the used reagents are cheap and easy-to-get, thus it save the synthesis cost, shorten the production cycle, improve the yield and product quality, and is suitable for mass production.

DESCRIPTION OF THE PREFERRED EMBODIMENTS

The present invention is further illustrated by the following specific examples. It should be understood, the following examples are only used for illustration of the present invention without intended to limit the scope of the invention.

The present invention is further illustrated by following examples but without any limitation.

Reference Example 1 Synthesis of tert-butyl 4-(3-chloro-2-formylphenyl)piperazine-1-carboxylate

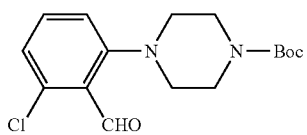 [SMILES: CC(C)(C)OC(=O)N1CCN(c2cccc(Cl)c2C=O)CC1]

2-chloro-6-fluorobenzaldehyde (500 mg, 3.15 mmol), tert-butyl piperazine-1-carboxylate (646 mg, 3.47 mmol) and potassium carbonate (2.18 g, 15.77 mmol) were added to N,N-dimethylformamide (5 mL) under a nitrogen atmosphere at room temperature. The mixture was stirred at 80° C. for 4 hours, cooled and filtered. Water (20 mL) was added thereto, then the mixture was extracted with ethyl acetate (3×5 mL). The organic layer was dried over anhydrous sodium sulfate, filtered to remove the drying agent, and concentrated. The resulting solid was slurried in petroleum ether (50 mL) for 1 h, filtered to obtain a pale yellow solid (750 mg, yield 75%).

$^1$HNMR (400 MHz, CDCl$_3$): δ 10.37 (s, 1H), 7.40 (t, 1H), 7.01 (d, 1H), 6.99 (d, 1H), 3.20 (m, 4H), 3.00 (s, 4H), 1.47 (s, 9H). ESI: [M+1]$^+$=325.8.

Reference Example 2 Synthesis of 4-(3-chloro-2-formylphenyl)piperazine-1-carbaldehyde

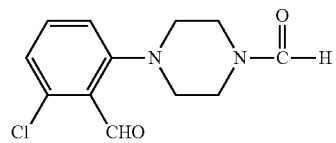 [SMILES: O=Cc1c(Cl)cccc1N1CCN(C=O)CC1]

2-chloro-6-fluorobenzaldehyde (500 mg, 3.15 mmol), 1-formyl piperazine (396 mg, 3.47 mmol) and potassium carbonate (2.18 g, 15.77 mmol) were added to DMF (5 mL) under a nitrogen atmosphere at room temperature. The mixture was stirred at 80° C. for 4 hours, cooled, added with water (20 mL) and extracted with ethyl acetate (3×5 mL). The organic layer was dried over anhydrous sodium sulfate and concentrated. The resulting solid was slurried in petroleum ether (50 mL) for 1 h, filtered to give a pale yellow solid (588 mg, yield 70%).

$^1$HNMR (400 MHz, CDCl$_3$): δ 10.45 (s, 1H), 8.13 (s, 1H), 7.44 (t, 1H), 7.18 (d, 1H), 7.02 (d, 1H), 3.80 (s, 2H), 36.4 (s, 2H), 3.10 (m, 4H). ESI: [M+1]$^+$=253.1.

Reference Example 3 Synthesis of 2-(4-acetylpiperazin-1-yl)-6-chlorobenzaldehyde

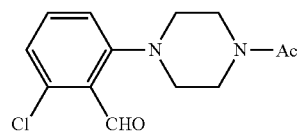 [SMILES: CC(=O)N1CCN(c2cccc(Cl)c2C=O)CC1]

2-chloro-6-fluorobenzaldehyde (500 mg, 3.15 mmol), 1-acetyl piperazine (444 mg, 3.47 mmol) and potassium carbonate (2.18 g, 15.77 mmol) were added to DMF (5 mL) under a nitrogen atmosphere at room temperature. The mixture was stirred at 80° C. for 4 hours, cooled and filtered. Water (20 mL) was added thereto, then the mixture was extracted with ethyl acetate (3×5 mL). The organic layer was dried over anhydrous sodium sulfate and concentrated. The resulting solid was slurried in petroleum ether (50 mL) for 1 h, filtered to obtain a pale yellow solid (588 mg, yield 70%).

$^1$HNMR (400 MHz, CDCl$_3$): δ 10.44 (s, 1H), 7.44 (t, 1H), 7.17 (d, 1H), 7.03 (d, 1H), 3.79 (bs, 4H), 3.10 (m, 4H), 2.18 (s, 3H). ESI: [M+1]$^+$=267.1.

Example 1 Synthesis of tert-butyl 4-(2-(ethoxycarbonyl)benzo[b]thiophen-4-yl)piperazine-1-carboxylate

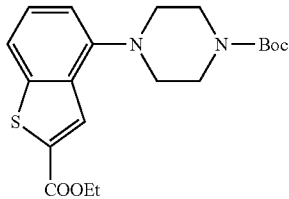 [SMILES: CCOC(=O)c1cc2c(N3CCN(C(=O)OC(C)(C)C)CC3)cccc2s1]

The product of Reference Example 1 (1.0 g, 3.08 mmol), ethyl mercaptoacetate (388 mg, 3.20 mmol) and potassium carbonate (1.38 g, 10 mmol) were added to N,N-dimethylformamide (5 mL) under a nitrogen atmosphere at room temperature. The mixture was stirred at 80° C. for 4 hours, cooled and filtered. Water (20 mL) was added thereto, then the mixture was extracted with ethyl acetate (3×5 mL). The organic layer was dried over anhydrous sodium sulfate and concentrated. The resulting solid was slurried in petroleum ether (50 mL) for 1 h, filtered to obtain a pale yellow solid (900 mg, yield 75%).

$^1$HNMR (400 MHz, CDCl$_3$): δ 8.40 (s, 1H), 7.58 (d, 1H), 7.37 (t, 1H), 6.95 (d, 1H), 4.44 (q, 2H), 3.64 (m, 4H), 3.15 (m, 4H). ESI: [M+1]$^+$=391.1.

Example 2 Synthesis of 4-(4-(tert-butoxycarbonyl)piperazin-1-yl)benzo[b]thiophene-2-carboxylic acid

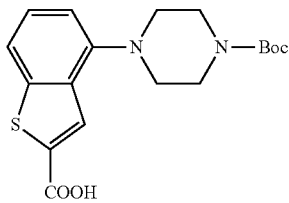 [SMILES: CC(C)(C)OC(=O)N1CCN(c2cccc3sc(C(=O)O)cc23)CC1]

The product of Example 1 (1.0 g, 2.5 mmol) was dissolved into 1,4-dioxane (5 mL), then 4N sodium hydroxide aqueous solution (1.8 mL, 7.2 mmol) was added thereto. The mixture was stirred at 80° C. for 3 h, cooled to room temperature. Water (5 mL) and ethyl acetate (10 mL) were added and the aqueous phase was separated. The pH of the aqueous phase was adjusted with 1N HCl to about 4.0 at 0° C. The precipitated solid was filtered, dried to obtain a pale yellow solid.

$^1$HNMR (400 MHz, DMSO-d$_6$): δ 7.98 (s, 1H), 7.64 (d, 1H), 7.42 (t, 1H), 6.95 (d, 1H), 3.53 (bs, 4H), 3.035 (bs, 4H). ESI: [M−1]$^-$=361.1.

Example 3 Synthesis of tert-butyl 4-(benzo[b]thiophen-4-yl)piperazine-1-carboxylate

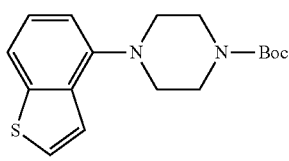 [SMILES: CC(C)(C)OC(=O)N1CCN(c2cccc3sccc23)CC1]

The product of Example 2 (20 g, 54 mmol), cuprous oxide (1 g, 7 mmol) were dissolved in quinoline (50 mL) and the mixture was stirred at 140° C. overnight. After cooling and filtering, the filtrate was added with water, and extracted with ethyl acetate. The organic phase was washed with 1N HCl to be weakly acidic, washed with saturated sodium bicarbonate aqueous solution, then subjected to silica gel column chromatography. The concentrated solid was slurried in petroleum ether to give an off-white solid (13 g, 70% yield).

$^1$HNMR (400 MHz, CDCl$_3$): δ 7.57 (d, 1H), 7.41 (s, 2H), 7.27 (t, 1H), 6.88 (d, 1H), 3.66 (m, 4H), 3.01 (m, 4H), 1.50 (s, 9H). ESI: [M+1]$^+$=319.1.

Example 4 Synthesis of tert-butyl 4-(benzo[b]thiophen-4-yl)piperazine-1-carboxylate

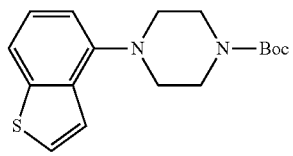 [SMILES: CC(C)(C)OC(=O)N1CCN(c2cccc3sccc23)CC1]

The product of Example 2 (500 mg, 1.35 mmol), silver carbonate (40 mg, 0.135 mmol) and acetic acid (8 mg) were dissolved in dimethyl sulfoxide (5 mL). The mixture was heated to 120° C. and stirred overnight, cooled and filtered. The filtrate was added with water, extracted with ethyl acetate. The organic layer was concentrated and subjected to column chromatography to give the target product.

$^1$HNMR (400 MHz, CDCl$_3$): δ 7.57 (d, 1H), 7.41 (s, 2H), 7.27 (t, 1H), 6.88 (d, 1H), 3.66 (m, 4H), 3.01 (m, 4H), 1.50 (s, 9H). ESI: [M+1]$^+$=319.1.

Example 5 Synthesis of 1-(benzo[b]thiophen-4-yl)piperazine hydrochloride

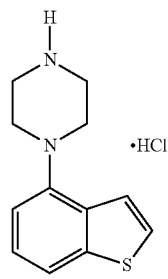 [SMILES: c1cc(N2CCNCC2)c2ccsc2c1 ; Cl]

The product of Example 3 (2 g, 6.2 mmol) was dissolved in dioxane (6 mL) and 4N HCl/dioxane solution (6 mL) was added. The mixture was stirred at room temperature for 3 h, and concentrated to dryness. The residue was slurried in ethyl acetate, filtered to obtain the target compound (1.3 g, yield 95%).

$^1$HNMR (400 MHz, DMSO-d$_6$): δ 9.46 (bs, 2H), 7.75 (d, 1H), 7.69 (d, 1H), 7.53 (t, 1H), 7.31 (t, 1H), 6.97 (t, 1H), 3.30 (bs, 8H). ESI: [M+1]$^+$=219.2.

Example 6 Synthesis of ethyl 4-(4-formylpiperazin-1-yl)benzo[b]thiophene-2-carboxylate

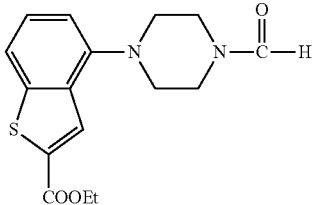 [SMILES: CCOC(=O)c1cc2c(N3CCN(C=O)CC3)cccc2s1]

The product of Reference Example 2 (1.0 g, 3.7 mmol), ethyl mercaptoacetate (410 mg, 3.80 mmol), potassium carbonate (1.38 g, 10 mmol) were added to DMF (5 mL) under a nitrogen atmosphere at room temperature, the mixture was stirred at 80° C. for 4 hours, cooled and added with water (20 mL), extracted with ethyl acetate (3×5 mL). The organic layer was dried over anhydrous sodium sulfate and concentrated. The resulting solid was slurried in petroleum ether (50 mL) for 1 h, filtered to give a pale yellow solid (1.0 g, yield 83%).

$^1$HNMR (400 MHz, CDCl3): δ 8.15 (d, 2H), 7.59 (d, 1H), 7.41 (t, 1H), 6.94 (d, 1H), 4.44 (q, 2H), 3.85 (t, 2H), 3.68 (t, 2H), 3.21-3.15 (m, 4H), 1.44 (t, 3H). ESI: [M+1]$^+$=319.1.

Example 7 Synthesis of 4-(4-formylpiperazin-1-yl)benzo[b]thiophene-2-carboxylic acid

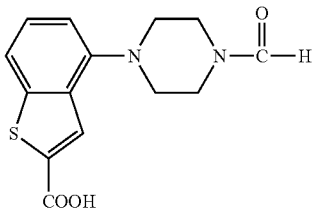 [SMILES: O=CN1CCN(c2cccc3sc(C(=O)O)cc23)CC1]

The product of Example 6 (1.0 g, 3.1 mmol) was dissolved in methanol (5 mL) and water (2 mL) and lithium hydroxide (420 mg, 10 mmol) was added. The mixture was stirred at room temperature for 5 h, added with water (5 mL) and extracted with ethyl acetate (10 mL). The aqueous phase was collected, the pH value was adjusted to about 4.0 with 1N HCl aqueous solution at 0° C. The precipitated solid was filtered and dried to give a pale yellow solid (510 mg, yield 56%).

ESI: [M−1]$^-$=289.1.

Example 8 Synthesis of 4-(benzo[b]thiophen-4-yl)piperazine-1-carbaldehyde

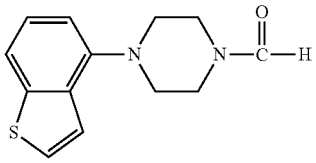 [SMILES: O=CN1CCN(c2cccc3sccc23)CC1]

The product of Example 7 (1.0 g, 3.4 mmol), cuprous oxide (50 mg) were dissolved in quinoline (5 mL), and the mixture was stirred at 140° C. overnight. After cooling and filtering, the filtrate was added with water, and extracted with ethyl acetate. The organic phase was washed with 1N HCl aqueous solution to be weakly acidic, washed with saturated sodium bicarbonate aqueous solution, concentrated and then subjected to silica gel column chromatography. The obtained solid was slurried in petroleum ether to give an off-white solid (520 mg, 62% yield).

$^1$HNMR (400 MHz, CDCl$_3$): δ 8.15 (s, 1H), 7.62 (d, 1H), 7.42 (m, 2H), 7.31 (t, 1H), 6.04 (d, 1H), 3.82 (t, 2H), 3.63 (t, 2H), 3.19-3.12 (m, 4H). ESI: [M+1]$^+$=247.1.

Example 9 Synthesis of 1-(benzo[b]thiophen-4-yl)piperazine hydrochloride

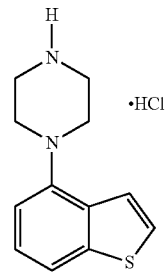

The product of Example 8 (500 mg) was dissolved in dioxane (2 mL) and 4N HCl/dioxane solution (3 mL) was added. The mixture was stirred at room temperature for 3 h, and concentrated to dryness. The residue was slurried in ethyl acetate, filtered to obtain the target compound (470 mg, yield 90%).

$^1$HNMR (400 MHz, DMSO-d$_6$): δ 9.46 (bs, 2H), 7.75 (d, 1H), 7.69 (d, 1H), 7.53 (t, 1H), 7.31 (t, 1H), 6.97 (t, 1H), 3.30 (bs, 8H). ESI: [M+1]$^+$=219.2.

Example 10 Synthesis of ethyl 4-(4-acetylpiperazin-1-yl)benzo[b]thiophene-2-carboxylate

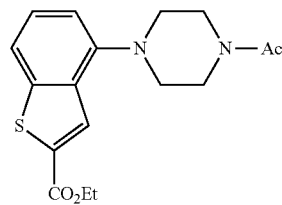 [SMILES: CCOC(=O)c1cc2c(N3CCN(C(C)=O)CC3)cccc2s1]

The product of Reference Example 3 (1.0 g, 3.74 mmol), ethyl mercaptoacetate (388 mg, 3.20 mmol), potassium carbonate (1.38 g, 10 mmol) were added to DMF (5 mL) under a nitrogen atmosphere at room temperature. The mixture was stirred at 80° C. for 4 hours, cooled and added with water (20 mL), extracted with ethyl acetate (3×5 mL). The organic layer was dried over anhydrous sodium sulfate and concentrated. The resulting solid was slurried in petroleum ether (50 mL) for 1 h, filtered to give a pale yellow solid (863 mg, yield 70%).

$^1$HNMR (400 MHz, CDCl$_3$): δ 8.17 (s, 1H), 7.60 (d, 1H), 7.42 (t, 1H), 7.01 (d, 1H), 4.44 (q, 2H), 3.94 (br, 2H), 3.80 (br, 2H), 3.21 (br, 4H), 2.19 (s, 3H), 1.44 (t, 3H).

ESI: [M+1]$^+$=333.3.

Example 11 Synthesis of 4-(4-acetylpiperazin-1-yl)benzo[b]thiophene-2-carboxylic acid

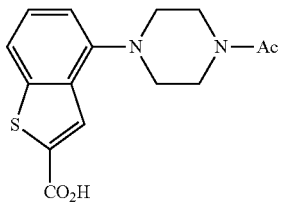 [SMILES: CC(=O)N1CCN(c2cccc3sc(C(=O)O)cc23)CC1]

The product of Example 10 (1.0 g, 3.0 mmol) was dissolved in methanol (5 mL) and water (2 mL), and lithium hydroxide (300 mg, 7.2 mmol) was added. The mixture was stirred at room temperature for 3 h, water (5 mL) and ethyl acetate (10 mL) were added, and the aqueous phase was separated. The pH value of the aqueous phase was adjusted to about 4.0 with 1N HCl aqueous solution at 0° C. The precipitated solid was filtered and dried to give a pale yellow solid (820 mg, yield 90%).
ESI: $[M-1]^-=303.1$.

Example 12 Synthesis of 1-(4-(benzo[b]thiophen-4-yl)piperazin-1-yl)ethanone

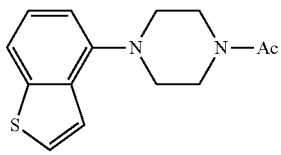 [SMILES: CC(=O)N1CCN(c2cccc3sccc23)CC1]

The product of Example 11 (1.0 g, 3.2 mmol), cuprous oxide (50 mg) were dissolved in quinoline (5 mL), and the mixture was stirred at 140° C. overnight. After cooling and filtering, the filtrate was added with water, and extracted with ethyl acetate. The organic phase was washed with 1N HCl aqueous solution to be weakly acidic, washed with saturated sodium bicarbonate aqueous solution, concentrated and then subjected to silica gel column chromatography. The obtained solid was slurried in petroleum ether to give an off-white solid (600 mg, 70% yield).
$^1$HNMR (400 MHz, DMSO-$d_6$): δ 7.95 (s, 1H), 7.65 (d, 1H), 7.41 (t, 1H) 6.95 (d, 1H), 3.69 (q, 4H), 3.10 (t, 2H), 3.02 (t, 2H), 2.06 (s, 3H). ESI: $[M+1]^+=261.1$.

Example 13 Synthesis of 1-(benzo[b]thiophen-4-yl)piperazine hydrochloride

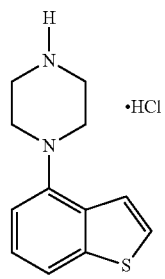 [SMILES: c1cc(N2CCNCC2)c2ccsc2c1 ; Cl]

The product of Example 12 (1 g) was dissolved in dioxane (6 mL), and 4N HCl/dioxane solution (6 mL) was added. The mixture was stirred at room temperature for 3 h and concentrated to dryness. The residue was slurried in ethyl acetate, filtered to obtain the product (870 mg, yield 90%).
$^1$HNMR (400 MHz, DMSO-$d_6$): δ 9.46 (bs, 2H), 7.75 (d, 1H), 7.69 (d, 1H), 7.53 (t, 1H), 7.31 (t, 1H), 6.97 (t, 1H), 3.30 (bs, 8H). ESI: $[M+1]^+=219.2$.

Example 14 Synthesis of 1-(benzo[b]thiophen-4-yl)piperazine

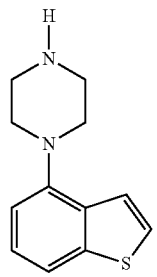 [SMILES: c1cc(N2CCNCC2)c2ccsc2c1]

The product of Example 2 (500 mg, 1.38 mmol) was dissolved in quinoline (3 mL) and cuprous oxide (20 mg) was added. The mixture was stirred at 140° C. for 2 h and at 240° C. for 3 h, then cooled to room temperature, then filtered, added with water, extracted with ethyl acetate. The organic layer was washed with saturated sodium bicarbonate aqueous solution, and subjected to silica gel column chromatography, and concentrated to give the target product.
$^1$HNMR (300 MHz, DMSO-$d_6$): δ 8.74 (bs, 1H), 7.75 (d, 1H), 7.69 (d, 1H), 7.51 (d, 1H), 7.31 (t, 1H), 6.95 (d, 1H), 3.24 (m, 8H). ESI: $[M+1]^+=219.2$.

Example 15 Synthesis of 4-(4-(4-((2-oxo-1,2,3,4-tetrahydroquinolin-7-yl)oxy)butyl)piperazin-1-yl)benzo[b]thiophene-2-carb oxylic acid

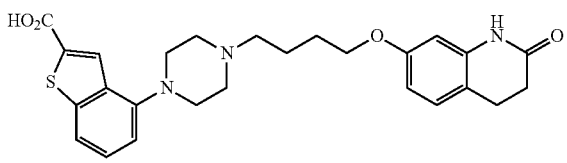 [SMILES: O=C1CCc2ccc(OCCCCN3CCN(c4cccc5sc(C(=O)O)cc45)CC3)cc2N1]

Ethyl 4-(4-(4-((2-oxo-1,2,3,4-tetrahydroquinolin-7-yl)oxy)butyl)piperazin-1-yl)benzo[b]thiophene-2-carb oxylate (300 mg, 0.59 mmol) was dissolved in methanol (3 mL) and water (1 mL) and lithium hydroxide (76 mg, 1.8 mmol) was added. The mixture was stirred at room temperature for 3 h, extracted with ethyl acetate and the aqueous phase was separated. After the pH value was adjusted to 4.0 with 1N hydrochloric acid, the aqueous phase was extracted with dichloromethane and methanol (10:1), the organic layer was concentrated to dryness to obtain a white solid (210 mg, 46% yield).
$^1$HNMR (400 MHz, DMSO-$d_6$): δ 10.01 (s, 1H), 7.88 (s, 1H), 7.61 (d, 1H), 7.38 (t, 1H), 7.03 (q, 1H), 6.93 (d, 1H), 6.48 (m, 2H), 3.92 (m, 4H), 3.35 (s, 4H), 2.84 (s, 4H), 2.77 (s, 2H), 2.62 (s, 2H), 1.72 (m, 4H), ESI: $[M-1]^-=478.3$.

Example 16 Synthesis of 7-(4-(4-(benzo[b]thio-phen-4-yl)piperazin-1-yl)butoxy)-3,4-dihydroquinolin-2(1H)-one

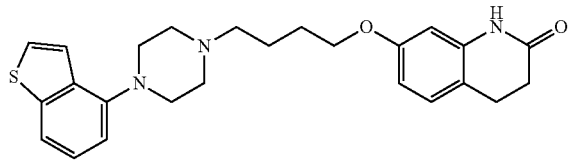 [SMILES: O=C1CCc2ccc(OCCCCN3CCN(c4cccc5sccc45)CC3)cc2N1]

The product of Example 15 (500 mg, 1.04 mmol), cuprous oxide (50 mg) were dissolved in quinoline (5 mL), and the mixture was stirred at 140° C. overnight. After cooling and filtering, water was added thereto, the mixture was extracted with ethyl acetate and the aqueous phase was separated. After the pH value was adjusted to 4.0 with 1N hydrochloric acid, the aqueous phase was extracted with dichloromethane and methanol (10:1), the organic layer was dried over anhydrous sodium sulfate, and subjected to silica gel column chromatography to give a solid (320 mg, yield 70%).

$^1$HNMR (400 MHz, DMSO-d$_6$): δ 10.00 (s, 1H), 7.69 (d, 1H), 7.61 (d, 1H), 7.40 (d, 1H), 7.27 (t, 1H), 7.04 (d, 1H), 6.89 (d, 1H), 6.50 (dd, 1H), 6.45 (d, 1H), 3.93 (t, 2H), 3.06 (br, 4H), 2.78 (t, 2H), 2.60 (br, 4H), 2.41 (t, 4H), 1.74 (t, 2H), 1.60 (t, 2H). ESI: [M+1]$^+$=436.3.

Example 17 Preparation of tert-butyl 4-(2-(ethoxy-carbonyl)benzo[b]thiophen-4-yl)piperazine-1-carboxylate

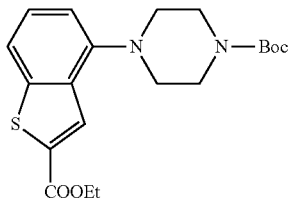

The product of Reference Example 1 (200 mg, 0.62 mmol), ethyl mercaptoacetate (0.081 ml, 0.74 mmol), potassium carbonate (342 mg, 2.48 mmol) were added to ethanol (5 mL) under a nitrogen atmosphere at room temperature. The mixture was stirred at 85° C. for 18 hours, concentrated, and subjected to column chromatography to obtain the target product (100 mg, yield 42%).

$^1$HNMR (400 MHz, CDCl$_3$): δ 8.40 (s, 1H), 7.58 (d, 1H), 7.37 (t, 1H), 6.95 (d, 1H), 4.44 (q, 2H), 3.64 (m, 4H), 3.15 (m, 4H). ESI: [M+1]$^+$=391.1.

Example 18 Preparation of tert-butyl 4-(2-(ethoxy-carbonyl)benzo[b]thiophen-4-yl)piperazine-1-carboxylate

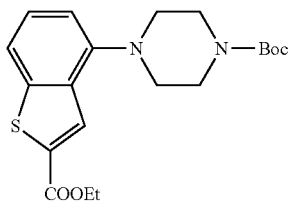 [SMILES: CCOC(=O)c1cc2c(N3CCN(C(=O)OC(C)(C)C)CC3)cccc2s1]

The product of Reference Example 1 (200 mg, 0.62 mmol), ethyl mercaptoacetate (0.081 ml, 0.74 mmol) and DIPEA (342 mg, 2.48 mmol) were added to DMF (5 mL) under a nitrogen atmosphere at room temperature. The mixture was stirred at 105° C. for 18 hours, then 1N HCl aqueous solution was added to adjust the pH=7. The mixture was extracted with methyl t-butyl ether, the ether layer was washed with saturated saline for three times, dried over anhydrous sodium sulfate, filtered to remove the drying agent, concentrated, and subjected to column chromatography to obtain the target product (170 mg, yield 71%).

$^1$HNMR (400 MHz, CDCl$_3$): δ 8.40 (s, 1H), 7.58 (d, 1H), 7.37 (t, 1H), 6.95 (d, 1H), 4.44 (q, 2H), 3.64 (m, 4H), 3.15 (m, 4H). ESI: [M+1]$^+$=391.1.

Example 19 Preparation of tert-butyl 4-(2-(ethoxy-carbonyl)benzo[b]thiophen-4-yl)piperazine-1-carboxylate

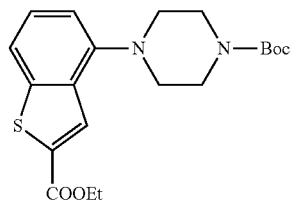

The product of Reference Example 1 (200 mg, 0.62 mmol), ethyl mercaptoacetate (0.081 ml, 0.74 mmol) and sodium hydroxide (100 mg, 2.48 mmol) were added to ethanol (5 mL) under a nitrogen atmosphere at room temperature. The mixture was stirred at 85° C. for 6 hours, concentrated and subjected to column chromatography to obtain the target product (70 mg, yield 30%). $^1$HNMR (400 MHz, CDCl$_3$): δ 8.40 (s, 1H), 7.58 (d, 1H), 7.37 (t, 1H), 6.95 (d, 1H), 4.44 (q, 2H), 3.64 (m, 4H), 3.15 (m, 4H). ESI: [M+1]$^+$=391.1.

Example 20 Preparation of 4-(piperazin-1-yl)benzo[b]thiophene-2-carboxylic acid hydrochloride

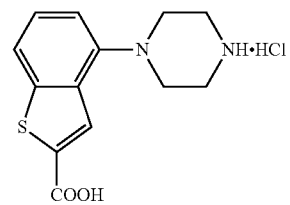

The product of Example 2 (200 mg, 0.55 mmol) was dissolved in THF (5 mL) and concentrated hydrochloric acid (0.5 mL) was added. The mixture was stirred at 50° C. for 6 h, cooled, added with methyl t-butyl ether (5 mL), filtered to give the target product (130 mg, 79% yield).

$^1$HNMR (400 MHz, DMSO-d$_6$): δ 9.46 (bs, 2H), 8.04 (s, 1H), 7.69 (d, 1H), 7.43 (t, 1H), 7.00 (d, 1H), 3.30 (bs, 8H). ESI: [M+1]$^+$=262.9.

Example 21 Preparation of 1-(benzo[b]thiophen-4-yl)piperazine hydrochloride

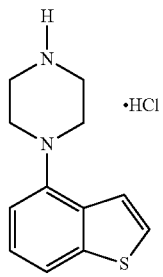 [SMILES: c1cc(N2CCNCC2)c2ccsc2c1 ; Cl]

The product of Example 20 (130 mg, 0.43 mmol) was added to diphenyl ether (3 mL) and the mixture was stirred at 260° C. for 0.5 h. The mixture was cooled and filtered to give the target product (60 mg, 55% yield).

$^1$HNMR (400 MHz, DMSO-$d_6$): δ 9.46 (bs, 2H), 7.75 (d, 1H), 7.69 (d, 1H), 7.53 (t, 1H), 7.31 (t, 1H), 6.97 (t, 1H), 3.30 (bs, 8H). ESI: [M+1]$^+$=219.2.

Example 22 Preparation of 4-(4-(tert-butoxycarbonyl)piperazin-1-yl)benzo[b]thiophene-2-carboxylic acid

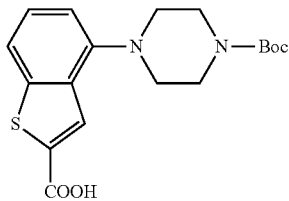

The product of Reference Example 1 (200 g, 0.62 mmol), mercaptoacetic acid (114 mg, 1.23 mmol) and sodium methoxide (133 mg, 2.45 mmol) were added to N,N-dimethylformamide (5 mL) under a nitrogen atmosphere at room temperature. The mixture was stirred at 105° C. for 18 hours, cooled, added with water, extracted with ethyl acetate and separated. The pH of the aqueous phase was adjusted to around 5, the precipitated solid was filtered and dried to obtain the target product (130 mg, yield 58%).

$^1$HNMR (400 MHz, DMSO-$d_6$): δ 7.98 (s, 1H), 7.64 (d, 1H), 7.42 (t, 1H), 6.95 (d, 1H), 3.53 (bs, 4H), 3.035 (bs, 4H). ESI: [M−1]$^−$=361.1.

Example 23 Preparation of 4-(4-(tert-butoxycarbonyl)piperazin-1-yl)benzo[b]thiophene-2-carboxylic acid

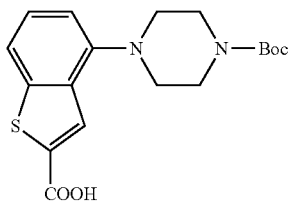 [SMILES: CC(C)(C)OC(=O)N1CCN(c2cccc3sc(C(=O)O)cc23)CC1]

The product of Reference Example 1 (200 g, 0.62 mmol), mercaptoacetic acid (114 mg, 1.23 mmol) and sodium hydroxide (99 mg, 2.45 mmol) were added to N,N-dimethylformamide (5 mL) under a nitrogen atmosphere at room temperature. The mixture was stirred at 105° C. for 18 hours, cooled, added with water, extracted with ethyl acetate and separated. The pH of the aqueous phase was adjusted to around 5, the precipitated solid was filtered and dried to obtain the target product (180 mg, yield 81%).

$^1$HNMR (400 MHz, DMSO-$d_6$): δ 7.98 (s, 1H), 7.64 (d, 1H), 7.42 (t, 1H), 6.95 (d, 1H), 3.53 (bs, 4H), 3.035 (bs, 4H). ESI: [M−1]$^−$=361.1.

Example 24 Preparation of ethyl 4-(4-(4-((2-oxo-1,2-dihydroquinolin-7-yl)oxy)butyl)piperazin-1-yl)benzo[b]thiophene-2-carboxylate

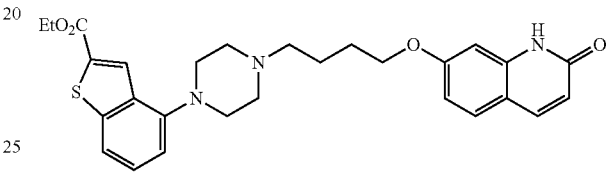

2-chloro-6-(4-(4-((2-oxo-1,2-dihydro-quinolin-7-yl)oxy)butyl)piperazin-1-yl) benzaldehyde (80 mg, 0.18 mmol) was dissolved in DMF (5 mL) and DIPEA (94 mg, 0.73 mmol) and ethyl mercaptoacetate (0.024 mL, 0.22 mmol) were added. The mixture was stirred at 110° C. for 16 hours, cooled, added with water, extracted with ethyl acetate. The ethyl acetate layer was washed with saturated brine, dried over anhydrous sodium sulfate, and subjected to silica gel column chromatography to give a solid (40 mg, 46% yield).

$^1$HNMR (400 MHz, DMSO-$d_6$): δ 11.69 (s, 1H), 11.24 (s, 1H), 8.09 (s, 1H), 7.81 (d, 1H), 7.74 (d, 1H), 7.57 (d, 1H), 7.48 (t, 1H), 7.04 (d, 1H), 6.82 (m, 2H), 6.30 (d, 1H), 4.32 (m, 4H), 4.06 (t, 2H), 3.67-3.16 (m, 8H), 1.96 (m, 2H), 1.84 (m, 2H), 1.32 (t, 3H). ESI: [M+1]$^+$=506.4.

Example 25 Synthesis of 4-(4-(4-((2-oxo-1,2,3,4-tetrahydroquinolin-7-yl)oxy)butyl)piperazin-1-yl)benzo[b]thiophene-2-carb oxylic acid

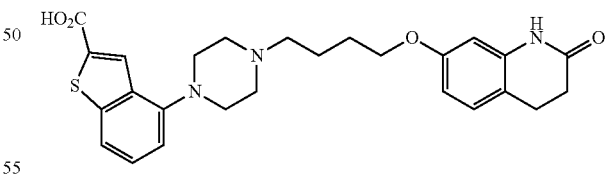

Ethyl 4-(4-(4-((2-oxo-1,2,3,4-tetrahydroquinolin-7-yl)oxy)butyl)piperazin-1-yl)benzo[b]thiophene-2-carb oxylate (100 mg, 0.19 mmol) was dissolved in acetic acid (3 mL) and concentrated hydrochloric acid (0.5 mL) and the mixture was stirred at 100° C. for 10 hours. The reaction mixture was poured into ice water, stirred for 10 min followed by filtration to obtain the target product (40 mg, 43% yield).

$^1$HNMR (400 MHz, DMSO-$d_6$): δ 10.01 (s, 1H), 7.88 (s, 1H), 7.61 (d, 1H), 7.38 (t, 1H), 7.03 (q, 1H), 6.93 (d, 1H), 6.48 (m, 2H), 3.92 (m, 4H), 3.35 (s, 4H), 2.84 (s, 4H), 2.77 (s, 2H), 2.62 (s, 2H), 1.72 (m, 4H), ESI: [M−1]$^−$=478.3.

Example 26 Preparation of 7-(4-(4-(benzo[b]thiophen-4-yl)piperazin-1-yl)butoxy)-3,4-dihydroquinolin-2(1H)-one

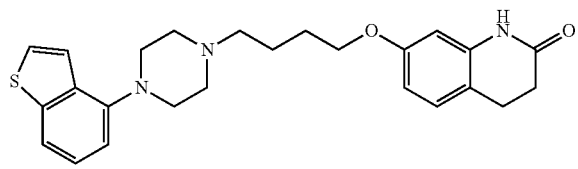 [SMILES: O=C1CCc2ccc(OCCCCN3CCN(c4cccc5sccc45)CC3)cc2N1]

The product of Example 25 (400 mg, 0.83 mmol) and silver carbonate (46 mg, 0.16 mmol) were dissolved in DMSO (5 mL) and acetic acid. The mixture was stirred at 120° C. overnight, cooled, added with water, extracted with ethyl acetate. The ethyl acetate layer was washed with saturated sodium bicarbonate and brine each for once, dried over anhydrous sodium sulfate, and subjected to silica gel column chromatography to give a solid (80 mg, 22% yield).

$^1$HNMR (400 MHz, DMSO-$d_6$): δ 10.00 (s, 1H), 7.69 (d, 1H), 7.61 (d, 1H), 7.40 (d, 1H), 7.27 (t, 1H), 7.04 (d, 1H), 6.89 (d, 1H), 6.50 (dd, 1H), 6.45 (d, 1H), 3.93 (t, 2H), 3.06 (br, 4H), 2.78 (t, 2H), 2.60 (br, 4H), 2.41 (t, 4H), 1.74 (t, 2H), 1.60 (t, 2H). ESI: [M+1]$^+$=436.3.

Example 27 Preparation of 74-(4-(4-((2-oxo-1,2-dihydroquinolin-7-yl)oxy)butyl)piperazin-1-yl)benzo[b]thiophene-2-carboxylic acid

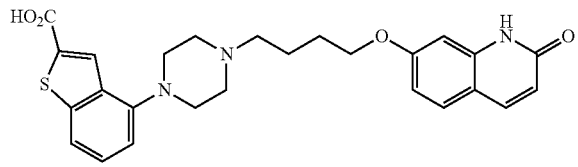 [SMILES: O=C(O)c1cc2c(N3CCN(CCCCOc4ccc5ccc(=O)[nH]c5c4)CC3)cccc2s1]

2-chloro-6-(4-(4-((2-oxo-1,2-dihydro-quinolin-7-yl)oxy)butyl)piperazin-1-yl) benzaldehyde (80 mg, 0.18 mmol) was dissolved in DMF (5 mL) and sodium hydroxide (29 mg, 0.73 mmol) and mercaptoacetic acid (0.025 mL, 0.36 mmol) were added. The mixture was stirred at 120° C. for 16 hours, cooled, added with water. The pH value of the aqueous phase was adjusted to around 5 with 11\T HCl aqueous solution. The mixture was extracted with ethyl acetate. The ethyl acetate layer was washed with saturated brine, dried over anhydrous sodium sulfate and subjected to silica gel column chromatography to give a solid (40 mg, 46% yield). ESI: [M+1]$^+$=478.0.

Example 28 Preparation of 4-(piperazin-1-yl)benzo[b]thiophene-2-carboxylic acid hydrochloride

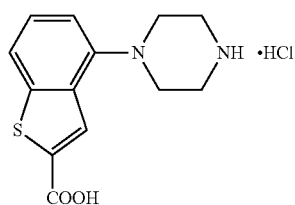 [SMILES: O=C(O)c1cc2c(N3CCNCC3)cccc2s1 ; Cl]

The product (100 mg, 0.25 mmol) of Example 17 was dissolved in acetic acid (3 mL) and concentrated hydrochloric acid (0.5 mL) and the mixture was stirred at 100° C. for 10 hours. The reaction mixture was poured into ice water, stirred for 10 min followed by filtration to obtain the target product (38 mg, 50% yield).

$^1$HNMR (400 MHz, DMSO-$d_6$): δ 9.46 (bs, 2H), 8.04 (s, 1H), 7.69 (d, 1H), 7.43 (t, 1H), 7.00 (d, 1H), 3.30 (bs, 8H). ESI: [M+1]$^+$=262.9.

The invention claimed is:
1. A compound having the structure represented by the following formula I:

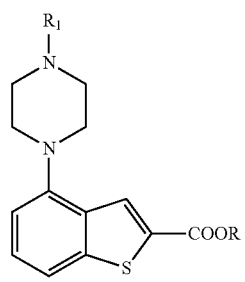

wherein, R is selected from the group consisting of linear or branched C1 to C6 alkyl, benzyl;
$R_1$ is t-butoxycarbonyl.

2. A preparation method for the compound according to claim 1, wherein the preparation method is conducted according to the following scheme 3:

Scheme 3:

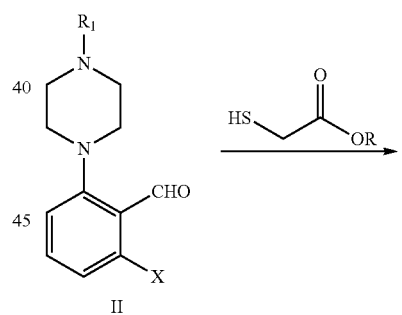

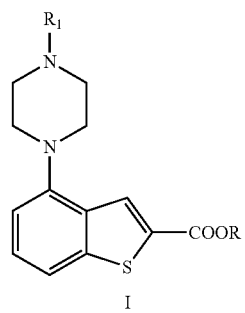

wherein, X is selected from the group consisting of fluorine, chlorine, bromine and iodine;
the definitions of R and $R_1$ are the same as those in the above claim 1;
the preparation method is conducted in the presence of a base;

the preparation method is conducted in a solvent;
the reaction time for the preparation method is 1 hour to 24 hours;
the reaction temperature for the preparation method is 0° C. to 150° C.

3. A compound represented by the formula III:

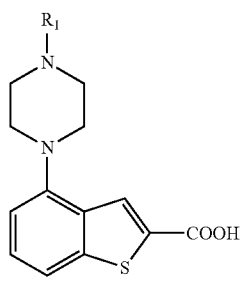

wherein, R1 is t-butoxycarbonyl.

4. A preparation method for the compound according to claim 3, wherein the preparation method is conducted according to the following scheme 4:

Scheme 4:

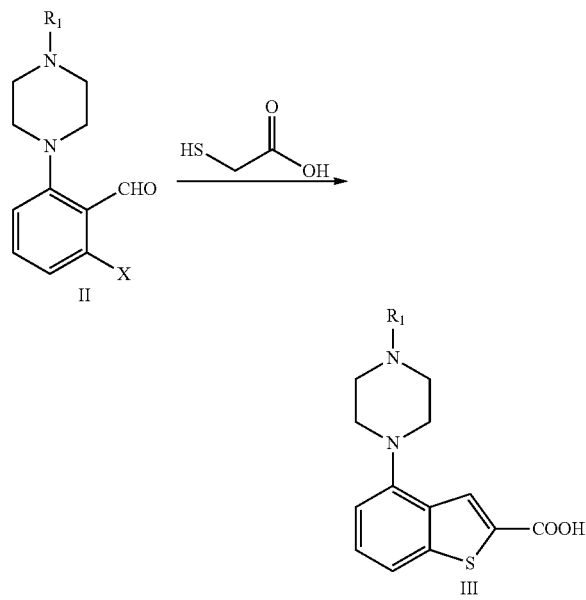

wherein, X is selected from the group consisting of fluorine, chlorine, bromine and iodine;
the definition of $R_1$ is the same as that in the claim 3;
the preparation method is conducted in the presence of a base;
the method is conducted in a solvent;
the reaction time for the method is 1 hour to 24 hours;
the reaction temperature for the method is 0° C. to 150° C.

5. The compound of claim 1, wherein,
R is selected from the group consisting of methyl, ethyl and t-butyl.

6. The preparation method of claim 2, wherein
the base is an inorganic base or an organic base;
the solvent is one or more selected from the group consisting of water, methanol, ethanol, n-propanol, isopropanol, n-butanol, isobutanol, tert-butanol, n-pentanol, isopentanol, ethylene glycol, propylene glycol, glycerol, N,N-dimethylformamide, dimethyl sulfoxide, tetrahydrofuran, acetonitrile, dioxane, N-methylpyrrolidone, dichloromethane, chloroform, ethylene glycol dimethyl ether, diethylene glycol dimethyl ether and ethylene glycol monomethyl ether;
the reaction time for the preparation method is 2 hours to 12 hours; and
the reaction temperature for the preparation method is from room temperature to 100° C.

7. The preparation method of claim 6, wherein
the inorganic base is one or more selected from the group consisting of sodium hydroxide, potassium hydroxide, strontium hydroxide, lithium hydroxide, barium hydroxide, calcium hydroxide, cesium hydroxide, sodium bicarbonate, potassium bicarbonate, potassium carbonate, sodium carbonate, strontium carbonate, cesium carbonate, sodium sulfide, and sodium hydride; and
the organic base is one or more selected from the group consisting of sodium alkoxide, potassium alkoxide, butyl lithium, 1,8-diazabicyclo [5,4,0]undec-7-ene, pyridine, quinoline, 4-dimethylaminopyridine and an organic amine.

8. The preparation method of claim 7, wherein
the sodium alkoxide is one or more selected from the group consisting of sodium methoxide, sodium ethoxide, sodium propoxide, sodium isopropoxide, sodium n-butoxide and sodium tert-butoxide;
the potassium alkoxide is one or more selected from the group consisting of potassium methoxide, potassium ethoxide, potassium propoxide, potassium isopropoxide, potassium n-butoxide and potassium tert-butoxide; and
the organic amine is one or more selected from the group consisting of triethylamine, diethylamine, tri-n-butylamine, tripropylamine, diisopropylamine and diisopropylethylamine.

9. The preparation method of claim 7, wherein,
the inorganic base is one or more selected from the group consisting of sodium hydroxide, potassium hydroxide, lithium hydroxide, sodium bicarbonate, potassium bicarbonate, potassium carbonate, sodium carbonate, strontium carbonate, sodium sulfide or sodium hydride, and
the organic base is one or more selected from the group consisting of sodium methoxide, sodium ethoxide, potassium t-butoxide, triethylamine, diethylamine, diisopropylamine and diisopropylethylamine.

10. The preparation method of claim 6, wherein,
the solvent is one or more selected from the group consisting of water, methanol, ethanol, N,N-dimethylformamide, dimethylsulfoxide, tetrahydrofuran, acetonitrile, dioxane and ethylene glycol dimethyl ether;
the reaction time for the preparation method is 2 hours to 12 hours; and
the reaction temperature for the preparation method is from room temperature to 100° C.

11. The preparation method of claim 4, wherein,
the base is an inorganic base or an organic base;
the solvent is one or more selected from the group consisting of water, methanol, ethanol, n-propanol, isopropanol, n-butanol, isobutanol, tert-butanol, n-pentanol, isopentanol, ethylene glycol, propylene glycol, glycerol, N,N-dimethylformamide, dimethyl sulfoxide, tetrahydrofuran, acetonitrile, dioxane, N-methylpyrrolidone, dichloromethane, chloroform, ethylene glycol dimethyl ether, diethylene glycol dimethyl ether and ethylene glycol monomethyl ether;

the reaction time for the preparation method is 2 hours to 12 hours; and the reaction temperature for the preparation method is from room temperature to 100° C.

12. The preparation method of claim 11, wherein, the inorganic base is one or more selected from the group consisting of sodium hydroxide, potassium hydroxide, strontium hydroxide, lithium hydroxide, barium hydroxide, calcium hydroxide, cesium hydroxide, sodium bicarbonate, potassium bicarbonate, potassium carbonate, sodium carbonate, strontium carbonate, cesium carbonate, sodium sulfide, and sodium hydride; and the organic base is one or more selected from the group consisting of sodium alkoxide, potassium alkoxide, butyl lithium, 1,8-diazabicyclo [5,4,0]undec-7-ene, pyridine, quinoline, 4-dimethylaminopyridine and an organic amine.

13. The preparation method of claim 12, wherein, the sodium alkoxide is one or more selected from the group consisting of sodium methoxide, sodium ethoxide, sodium propoxide, sodium isopropoxide, sodium n-butoxide and sodium tert-butoxide;

the potassium alkoxide is one or more selected from the group consisting of potassium methoxide, potassium ethoxide, potassium propoxide, potassium isopropoxide, potassium n-butoxide and potassium tert-butoxide, and the organic amine is one or more selected from the group consisting of triethylamine, diethylamine, tri-n-butylamine, tripropylamine, diisopropylamine and diisopropylethylamine.

14. The preparation method of claim 12, wherein, the inorganic base is selected from the group consisting of sodium hydroxide, potassium hydroxide, lithium hydroxide, sodium bicarbonate, potassium bicarbonate, potassium carbonate, sodium carbonate, strontium carbonate, sodium sulfide or sodium hydride, and the organic base is selected from the group consisting of sodium methoxide, sodium ethoxide, potassium t-butoxide, triethylamine, diethylamine, diisopropylamine and diisopropylethylamine.

15. The preparation method of claim 11, wherein, the solvent is one or more selected from the group consisting of water, methanol, ethanol, N,N-dimethylformamide, dimethylsulfoxide, tetrahydrofuran, acetonitrile, dioxane and ethylene glycol dimethyl ether;

the reaction time for the preparation method is 2 hours to 12 hours; and the reaction temperature for the preparation method is from room temperature to 100° C.

* * * * *